United States Patent [19]

Boelens et al.

[11] 4,124,771

[45] Nov. 7, 1978

[54] 8-ALLYL-8-HYDROXYTRICYCLO-[5,2,1,$0^{2,6}$] DECANE

[75] Inventors: Harmannus Boelens, Huizen; Hendrik J. Wobben, Naarden, both of Netherlands

[73] Assignee: Naarden International, N.V., Naarden-Bussum, Netherlands

[21] Appl. No.: 826,768

[22] Filed: Aug. 22, 1977

Related U.S. Application Data

[62] Division of Ser. No. 635,213, Nov. 25, 1975, Pat. No. 4,057,516.

[30] Foreign Application Priority Data

Nov. 27, 1974 [NL] Netherlands ........................ 7415485

[51] Int. Cl.[2] .............................................. C07C 35/22

[52] U.S. Cl. ...................................... 568/817; 252/522

[58] Field of Search .................................... 260/617 G

[56] References Cited

U.S. PATENT DOCUMENTS

| | | | |
|---|---|---|---|
| 2,875,244 | 2/1959 | Bartlett et al. | 260/617 G |
| 3,407,225 | 10/1968 | Dunkel | 260/617 G |
| 3,417,132 | 12/1968 | Dunkel | 260/617 G |
| 3,524,890 | 8/1970 | Cox | 260/617 G |
| 3,662,008 | 5/1972 | Krelzchmar et al. | 260/617 G |
| 3,662,010 | 5/1972 | Legendy et al. | 260/617 G |
| 4,076,748 | 2/1978 | Hoffman et al. | 260/617 G |

*Primary Examiner*—Norman Morgenstern
*Attorney, Agent, or Firm*—Stevens, Davis, Miller & Mosher

[57] ABSTRACT

8-Allyl-8-hydroxytricyclo[5,2,1,$0^{2,6}$] decane.

1 Claim, No Drawings

8-ALLYL-8-HYDROXYTRICYCLO-[5,2,1,$0^{2,6}$] DECANE

This is a Division of application Ser. No. 635,213 filed Nov. 25, 1975, now U.S. Pat. No. 4057516.

This invention relates to a new compound 8-allyl-8-hydroxytricyclo[5,2,1,$0^{2,6}$] decane as a starting material to be used in perfumery. More specifically the invention relates to 8-allyl-8-hydroxytricyclo-[5,2,1,$0^{2,6}$] decane for imparting an improved odor of castoreum to perfume compositions and perfumed materials.

In perfumery many natural materials are used. However, these materials suffer from the disadvantage of not always being available in sufficient quantities. Moreover they are often expensive and not of consistent quality. The use of certain animal materials also may be objected to because of the danger of extinction of the animal species under consideration, or because collection of the product is annoying to the animal. So it is advantageous to prepare or compound synthetic perfume materials whose odor properties approach those of the natural materials as closely as possible. Castoreum is an animal material derived from beavers (Castor fiber). It is very popular for use in perfumery but is expensive and hard to obtain for the reasons set forth above.

In all attempts to imitate the odor of castoreum, compounds were used that are known to be constituents of natural castoreum (see for example: E. Lederer, Odeurs et Parfums des Animaux in "Fortschritte der Chemie organischer Naturstoffe" VI (1949), p. 112). However, an additional amount of natural castoreum was always necessary to obtain a high quality castoreum odor in perfume compositions (see for example: F. Cole, "Le Livre du Parfumeur", Casterman, Paris (1951), p. 421).

It was found that a very natural and satisfactory castoreum odor can be imparted to perfume compositions, without using any natural castoreum, by adding 8-allyl-8-hydroxytricyclo [5,2,1,$0^{2,6}$]decane of the formula

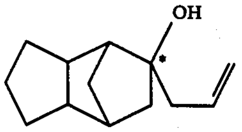

to other components commonly used in preparing perfume compositions.

The phrase "perfume composition" is used to mean a mixture consisting of for example essential oils, hydrocarbons, alcohols, esters, acids, aldehydes, ketones and other odorous and non-odorous substances. This mixture may be used as such, or after dilution with a suitable solvent (e.g. alcohol) to impart a desired odor to products like detergents, soaps, creams, lotions and other cosmetics.

The compound 8-allyl-8-hydroxytricyclo [5,2,1,$0^{2,6}$]decane is prepared in a way known per se, from tricyclo [5,2,1,$0^{2,6}$]decan-8-one and an allylmagnesium halogenide. Both stereo-isomeric ketones (endo and exo) will undergo this Grignard reaction and both will yield two new stereo-isomers because of the introduction of a new asymmetric center (indicated by *). It is possible to separate the four stereo-isomers by methods known per se, but this is not necessary for practicing the invention. So for economical reasons the use of the mixture of isomers is preferred. The compound 8-allyl-8-hydroxytricyclo[5,2,1,$0^{2,6}$] decane may be used separately or together with o-hydroxybenzyl ethyl ether in preparing a synthetic castoreum, if desired in conjunction with compounds known to be components of natural castoreum (e.g. benzoic acid, salicylic acid, their methyl and ethyl esters, cresol and other phenolic compounds, acetophenone, etc.). The addition of o-hydroxybenzyl ethyl ether accentuates the phenolic character and improves the odor or a synthetic castoreum when used in an amount of 1000 ppm by weight or more. On the other hand 8-allyl-8-hydroxytricyclo-[5,2,1,$0^{2,6}$] decane has a more sweet animal character and improves the odor of a synthetic castoreum when used in amounts of 100 ppm by weight or more. Especially the combination of o-hydroxybenzyl ethyl ether and 8-allyl-8-hydroxytricyclo[5,2,1,$0^{2,6}$] decane makes it possible to obtain a very near approach to the odor of natural castoreum. With this combination a synthetic castoreum may be prepared which is so close to nature that it is able to substitute natural castoreum in any desired application. It is also possible to use 8-allyl-8-hydroxytricyclo[5,2,1,$0^{2,6}$] decane either separately or in combination with o-hydroxybenzyl ethyl ether, directly in a perfume composition to impart a castoreum effect.

The weight ratio of o-hydroxybenzyl ethyl ether to 8-allyl-8-hydroxytricyclo [5,2,1,$0^{2,6}$] decane if used together depends on the desired effect. In general it will be between 300:1 and 1:5. Preferably a ratio between 30:1 and 1:1 is used. As far as the use in synthetic castoreum is concerned, one has to keep in mind the minimum effective amounts of both compounds as described above. When using such a synthetic castoreum in a perfume composition, the concentrations of o-hydroxybenzyl ethyl ether and 8-allyl-8-hydroxytricyclo [5,2,1,$0^{2,6}$] decane in the final composition may be much lower, depending on the amount of synthetic castoreum used in this composition.

The following examples are illustrative for the preparation of 8-allyl-8-hydroxytricyclo [5,2,1,$0^{2,6}$] decane and the use of o-hydroxybenzyl ethyl ether and 8-allyl-8-hydroxytricyclo-[5,2,1,$0^{2,6}$] decane as perfume components.

EXAMPLE 1

Preparation of 8-allyl-8-hydroxytricyclo [5,2,1,$0^{2,6}$] decane.

In a one liter reaction vessel, equipped with a stirrer, a cooler and a dropping funnel, 26.4 g magnesium, 100 g tetrahydrofurane and 1 g allyl chloride were heated to about 40° C. to start the reaction. A mixture of 76.5 g allyl chloride, 250 g tetrahydrofurane and 150 g tricyclo [5,2,1,$0^{2,6}$] decan-8-one was added in 4 hours, keeping the temperature at 35°-40° C. The reaction mixture was stirred for an additional 30 minutes and subsequently poured into a mixture of 600 g of ice and 80 g of acetic acid. The layers were separated and the water layer extracted twice with toluene. The combined organic layers were washed with 5% soda solution until alkaline and subsequently with water until neutral. The organic solvent was removed by distillation under reduced pressure. The residue was distilled on a Vigreux head at 2 mm.Hg. The fraction boiling between 93°and 95° C. was collected. Yield: 80%, $n_D^{20}$: 1.5154.

EXAMPLE 2

A synthetic castoreum was prepared by mixing the following ingredients (amounts given in parts by weight):

738 benzoic acid
50 farnesol
20 farnesyl acetate
10 farnesyl isobutyrate
15 o-cresol
5 p-cresol
4 m-cresol
6 salicylic acid
2 borneol
1 eugenylphenyl acetate
25 ethyl benzoate
10 methyl benzoate
6 methyl phenyl carbinol
4 acetophenone
2 pentanoic acid
2 butanoic acid
900 This mixture was called mixture A.

The following mixtures were prepared:

Mixture B:
900 parts by weight of mixture A
85 parts by weight of o-hydroxybenzyl ethyl ether
985 parts.

Mixture C:
900 parts by weight of mixture A
15 parts by weight of 8-allyl-8-hydroxytricyclo-[5,2,1,$0^{2,6}$] decane
915 parts.

Mixture D:
900 parts by weight of mixture A.
85 parts by weight of o-hydroxybenzyl ethyl ether
15 parts by weight of 8-allyl-8-hydroxitricyclo-(5,2,1,$0^{2,6}$] decane
1000 parts.

The mixtures A, B, C and D were compared by 7 trained perfumers. B and C were unanimously preferred over A. Two experts preferred C over B, the others preferred B over C. However D was judged unanimously as the mixture with the best and most natural castoreum odor.

EXAMPLE 3

By mixing the following ingredients a men's cologne concentrate was prepared using the synthetic castoreum mixture D of Example 2 (amounts given in parts by weight):

15 musk-ketone
15 Musk Rl ®(11-oxa-hexadecanolide)
10 tonka absolute
10 heliotropine
20 benzylisoeugenol
15 mousse absolute
10 galbarum resin
15 benzoe resin Siam
75 lemon oil Italian
200 bergemot oil
10 verveic oil
100 sandalwood oil E.I.
100 α-isomethylionone
50 cedarwood oil Virginia
25 clove bud oil
50 Rosana NB 131*
50 Jasmin NB 133*
50 vetiveryl acetate
25 ylang ylang I
10 geranium oil Bourbon
10 basil oil
10 angelica root oil
10 clary sage oil
50 lavender oil 45-47%
30 lauric aldehyde, 10% in diethyl phthalate
10 civette absolute, 10% in ethanol
25 mixture D of Example 2, 10% in benzylalcohol.
1000 ® registered trade mark of Naarden International

* perfume base of Naarden International.

What is claimed is:

1. 8-Allyl-8-hydroxytricyclo (5,2,1,$0^{2,6}$) decane.

* * * * *